United States Patent
Tarone et al.

(10) Patent No.: US 7,025,717 B2
(45) Date of Patent: Apr. 11, 2006

(54) SEMI-AUTOMATIC NEEDLE LOADER

(75) Inventors: Theodore T. Tarone, West Palm Beach, FL (US); Mario LaCasse, Palm Beach Gardens, FL (US)

(73) Assignee: Bard Brachytherapy, Inc., Carol Stream, IL (US)

( * ) Notice: Subject to any disclaimer, the term of this patent is extended or adjusted under 35 U.S.C. 154(b) by 537 days.

(21) Appl. No.: 10/161,239

(22) Filed: May 31, 2002

(65) Prior Publication Data

US 2003/0028067 A1    Feb. 6, 2003

Related U.S. Application Data

(60) Provisional application No. 60/309,720, filed on Aug. 2, 2001.

(51) Int. Cl.
*A61N 5/00* (2006.01)
*A61M 31/00* (2006.01)

(52) U.S. Cl. .......................................................... 600/7

(58) Field of Classification Search .................. 600/1–8
See application file for complete search history.

(56) References Cited

U.S. PATENT DOCUMENTS

| 5,860,909 | A | * | 1/1999 | Mick et al. ..................... 600/7 |
| 6,013,020 | A | * | 1/2000 | Meloul et al. ................. 600/7 |
| 6,213,932 | B1 | * | 4/2001 | Schmidt ......................... 600/7 |
| 6,358,195 | B1 | * | 3/2002 | Green et al. ................... 600/7 |
| 6,561,967 | B1 | * | 5/2003 | Schmidt ......................... 600/7 |

* cited by examiner

*Primary Examiner*—Samuel G. Gilbert
(74) *Attorney, Agent, or Firm*—Stroock & Stroock & Lavan LLP

(57) ABSTRACT

A semi-automatic needle loader assembly is disclosed that includes a setting group for positioning at least one of an isotope seed and a spacer, a loading group operatively engaging the setting group for depositing the at least one of an isotope seed and a spacer, a viewing member for visualizing the at least one of an isotope seed and a spacer, and a needle holding group positioned to pass the at least one of an isotope seed and a spacer to a needle assembly.

31 Claims, 7 Drawing Sheets

SEMI-AUTOMATIC NEEDLE LOADER

CROSS-REFERENCES TO RELATED APPLICATIONS

This application claims the benefit of U.S. Provisional Application Ser. No. 60/309,720, filed on Aug. 2, 2001, entitled SEMI-AUTOMATIC NEEDLE LOADER.

TECHNICAL FIELD

In general, the present invention relates to surgical tools. More particularly, the present invention relates to an apparatus that semi-automatically and alternatively loads radioactive isotope seeds and biocompatible spacers into a needle for insertion into a prostate gland or other internal organ.

BACKGROUND

Brachytherapy is a form of cancer treatment in which a radioactive energy source is placed into or adjacent to a malignant tumor. Generally, brachytherapy can be divided into two categories: high dose rate (HDR); and low dose rate (LDR). In HDR brachytherapy, a radioactive energy source with high activity is placed into or adjacent to the malignant tumor for a predefined period of time. Conversely, LDR brachytherapy entails the placement of a low activity radioactive energy source into or adjacent to the malignant tumor for an indeterminate period of time.

In LDR brachytherapy, radioactive isotopes are used as the radioactive energy sources. Some of the more common radioactive isotopes used in LDR brachytherapy include Iodine-125, Palladium-103, Gold-198, Ytterbium-169, and Iridium-192. These isotopes are typically packaged in a housing constructed of a lightweight and durable material, such as titanium, and are commonly referred to as isotope seeds. The dimensions of the isotope seeds can be extremely variable both in diameter and in length. The radioactive isotopes commonly used in LDR brachytherapy are selected for their low energy and relatively short half-life. Low energy sources provide for a limited tissue penetration by the emitted radiation, so that the radiation's effects are limited to the tumor without substantially affecting adjacent normal tissue. A short half-life is advantageous in that the dose of radiation that is delivered depletes in a reasonably short period of time.

The area of therapeutic effect for Iodine-125 and Palladium-103 is limited to a sphere approximately 1 cm in diameter around the isotope seed. As a result, a three-dimensional array of isotope seeds is commonly used to treat a tumor. In LDR brachytherapy of prostate cancer, a multitude of isotope seeds is typically used. Since solid tumors, like those found in prostate cancer, are perceived to be diffuse, the entire organ is targeted for therapy.

In order to place isotope seeds into the aforementioned three-dimensional array, needles, using a two-dimensional grid pattern in conjunction with longitudinal spacing, can deliver isotope seeds. The two dimensional grid is frequently defined by a needle guide, called a template. The template is provided with a plurality of holes that provide guidance for the longitudinal progression of the needles, thus insuring their desired two-dimensional position within the tumor. After the two-dimensional needle array is positioned within the tumor, the isotope seeds are deposited along the longitudinal axis of each needle.

Proper spacing of the isotope seeds along the longitudinal axis of the needle is accomplished through the use of biocompatible spacers further deposited between the isotope seeds. The use of spacers also serves to maintain the low energy effect on the prostate by maintaining a distance between the isotope seeds. The spacers and isotope seeds are alternately loaded into the needle prior to placement of the needle into the tumor. Upon placing the needle into the tumor, a cannula is engaged to maintain the position of the line of isotope seeds and spacers as the needle is withdrawn. This yields a line of isotope seeds in their proper longitudinal position. This process is repeated at the other two dimensional grid coordinates, thus forming the desired three dimensional array of isotope seeds.

An improved version of this procedure, as disclosed in U.S. Pat. No. 6,213,932, includes transparent plastic seed cartridges, detachably connected to the applicator, for holding a plurality of radioactive isotope seeds. This version enabled a surgeon to visually ascertain the number of spacers within a cartridge, thereby eliminating the guesswork previously involved in determining the number of remaining isotope seeds, greatly reducing the time required to load a needle.

A device that includes a cartridge having a plurality of individual isotope seeds, known as the Mick™ applicator system, registered to Mick Radio-Nuclear Instruments, Inc., is currently in widespread use. The cartridge retains a large number of individual isotope seeds that have been loaded therein at a separate facility. Additionally, isotope seeds can also be loaded into the cartridge at the hospital or at a nuclear pharmacy, thereby eliminating the time and cost requirements of loading individual isotope seeds in an operating room.

In the prior art, a seed-containing cartridge is attached to an applicator in a manner substantially similar to the way a magazine is attached to a firearm. The cartridge is spring-loaded to force one isotope seed at a time into a seed discharge chamber that further retains a single isotope seed for insertion into a needle. A special hollow needle is connected to the needle holder of a distal end of the applicator. A push rod is inserted into a distal end of the applicator and pushed directionally in a proximal-to-distal direction. The distal end of the push rod engages an isotope seed in the seed discharge chamber and drives the isotope seed into the hollow interior of the special needle and then out of the distal end of the needle into the prostate. The surgeon then extracts the needle to a predetermined distance, withdraws the plunger rod to a position on the proximal end of the seed discharge chamber so that an additional isotope seed can enter the chamber from the cartridge. Subsequent isotope seeds are then introduced into the needle, and then prostate, in an identical manner.

Although the Mick™ applicator system eliminates the risk of dropping individual isotope seeds in an operating room, it increases the amount of time required to implant a multitude of isotope seeds into the prostate because of the inability to inject more than one seed at a time. Further advances in this technique have additionally resulted in a reduction of the guesswork required by the surgical staff to determine the number of isotope seeds in a cartridge. However, these systems do not provide for either an identical loading system for spacers or for a system for visualizing the order of isotope seeds and spacers to be loaded into a needle.

Thus, there is a need for an improved applicator system that semi-automatically and sequentially loads radioactive isotope seeds and biocompatible spacers and that enables a surgeon to visually ascertain the number and sequence of isotope seeds and spacers within a cartridge.

SUMMARY OF THE INVENTION

The present invention eliminates the above-mentioned needs for an improved version of the brachytherapy procedure for cancer treatment by providing a device and method for the semiautomatic and sequential loading of at least one isotope seed followed by at least one biocompatible spacers and that further enables a surgeon to visually ascertain the number and sequence of isotope seeds and spacers within a cartridge.

The present invention is directed to a semi-automatic needle loader assembly that includes a setting group, a loading group, a viewing member, and a needle holding group. The setting group further includes a handle, a push rod, and a stop block member. The handle is operatively engaged to the push rod, which is slidable within a push rod guide member. The push rod guide member passes through the stop block member, itself slidably mounted to a mounting plate. The stop block member can slidably select a number from a predefined series, indicating a number of radioactive isotope seeds or biocompatible spacers. Furthermore, the stop block member functions as the distal endpoint for the handle that is in operative engagement with the push rod.

The loading group of the assembly further includes a loading block and an indexing member. The loading block accommodates a slidable cartridge holder that can hold a plurality of cartridges, including at least one seed cartridge and at least one spacer cartridge. Further, the loading block includes an alignment visualizer to provide visual confirmation of a selected cartridge. The indexing member is spring-loaded and operatively engages the slidable cartridge holder to select at least one cartridge from the plurality of cartridges. The viewing member of the present invention further includes a body, a visualization plate, and a needle holder securement. The body also includes a demarcation gauge that permits identification of the number of isotope seeds and spacers to be loaded. The body further accommodates the push rod guide member and allows for the fixing of the visualization plate. The visualization plate allows for visualization of the demarcation gauge while functioning as a radiation shield. Additionally, the needle holder securement of the assembly accommodates the needle holder group that is composed of a needle holder flange, a needle holder hub, and a needle lock. The needle holder flange is affixed to the needle holder securement and accommodates the needle holder hub that further accommodates a needle. The needle lock secures the needle.

The present invention is further directed to a method for semi-automatically and sequentially loading radioactive seed units and biocompatible spacer units into a brachytherapy device where a plurality of cartridges with a plurality of aligned units is provided and is in operative engagement with a cartridge holder. A first cartridge is selected from the plurality of cartridges, and at least one first aligned unit of the first cartridge is deposited into a unit channel. The at least one first aligned unit of the first cartridge is driven along the unit channel to a first predetermined point. A second cartridge is then selected from the plurality of cartridges, with at least one second aligned unit of the second cartridge deposited into the unit channel. The at least one second aligned unit of the second cartridge is also driven along the unit channel to a second predetermined point by the push rod. The at least one first aligned unit of the first cartridge and the at least one second aligned unit of the second cartridge are subsequently inserted into a needle for insertion into biological tissue.

DETAILED DESCRIPTION

Figure 1:
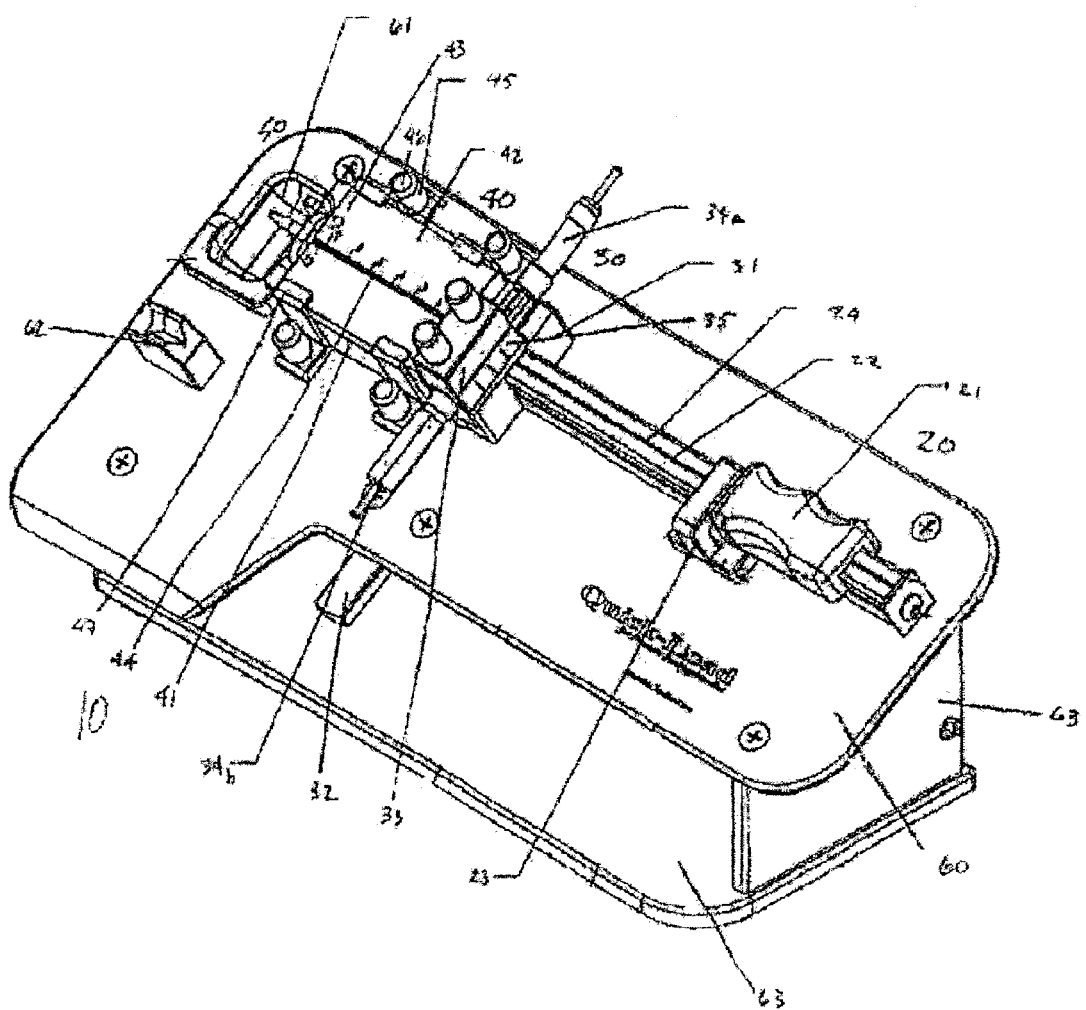
FIG. 1 is an illustration of the preferred embodiment of the present invention.

Referring now to FIG. 1, a preferred embodiment of the present invention is illustrated as the semi-automatic needle loader assembly 10. The semi-automatic needle loader assembly 10 includes a setting group 20, a loading group 30, a viewing member 40, and a needle holding group 50. The setting group 20 further includes a handle 21, a push rod 22, and a stop block member 23. The handle 21 is operatively engaged to the push rod 22, which is slidable within a push rod guide member 24. The push rod guide member 24 passes through the stop block member 23, itself slidably mounted to a mounting plate 60. Mounting plate 60 includes receiving tray 61 and stylet inserting block 62. The receiving tray 61 is adapted to collect isotope seeds and spacers that unintentionally fall out of the needle holding group 50. Stylet inserting block 62 is used for placing a stylet in a resting position. Additionally, the mounting plate 60 may itself be mounted to a series of receiving plates 63 to obtain an elevated position for mounting plate 60. The stop block member 23 slidably selects a number from a predefined series, indicating a number of radioactive isotope seeds or biocompatible spacers. Furthermore, the stop block member 23 functions as the distal endpoint for the handle 21 that is in operative engagement with the push rod 22.

Figure 2:
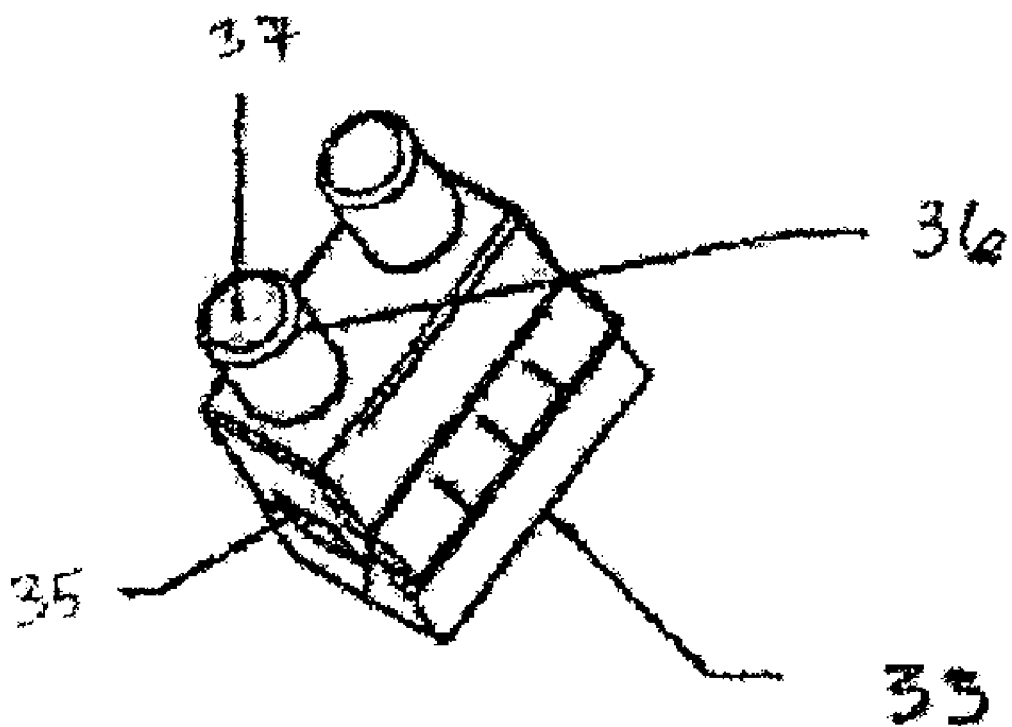
FIG. 2 is an illustration of the loading block of the present invention illustrated in FIG. 1.

The loading group 30 of the assembly further includes a loading block 31 and an indexing member 32. The loading block 31 accommodates a slidable cartridge holder 33 that can hold a plurality of cartridges 34, including at least one seed cartridge and at least one spacer cartridge. Further, the loading block 31 includes an alignment visualizer 35 to provide visual confirmation of a selected cartridge. As illustrated in FIG. 2, slidable cartridge holder 33 secures cartridges 34 with cartridge clamps 35, which are tightened with screws 36 and retaining clips 37.

Figure 3:
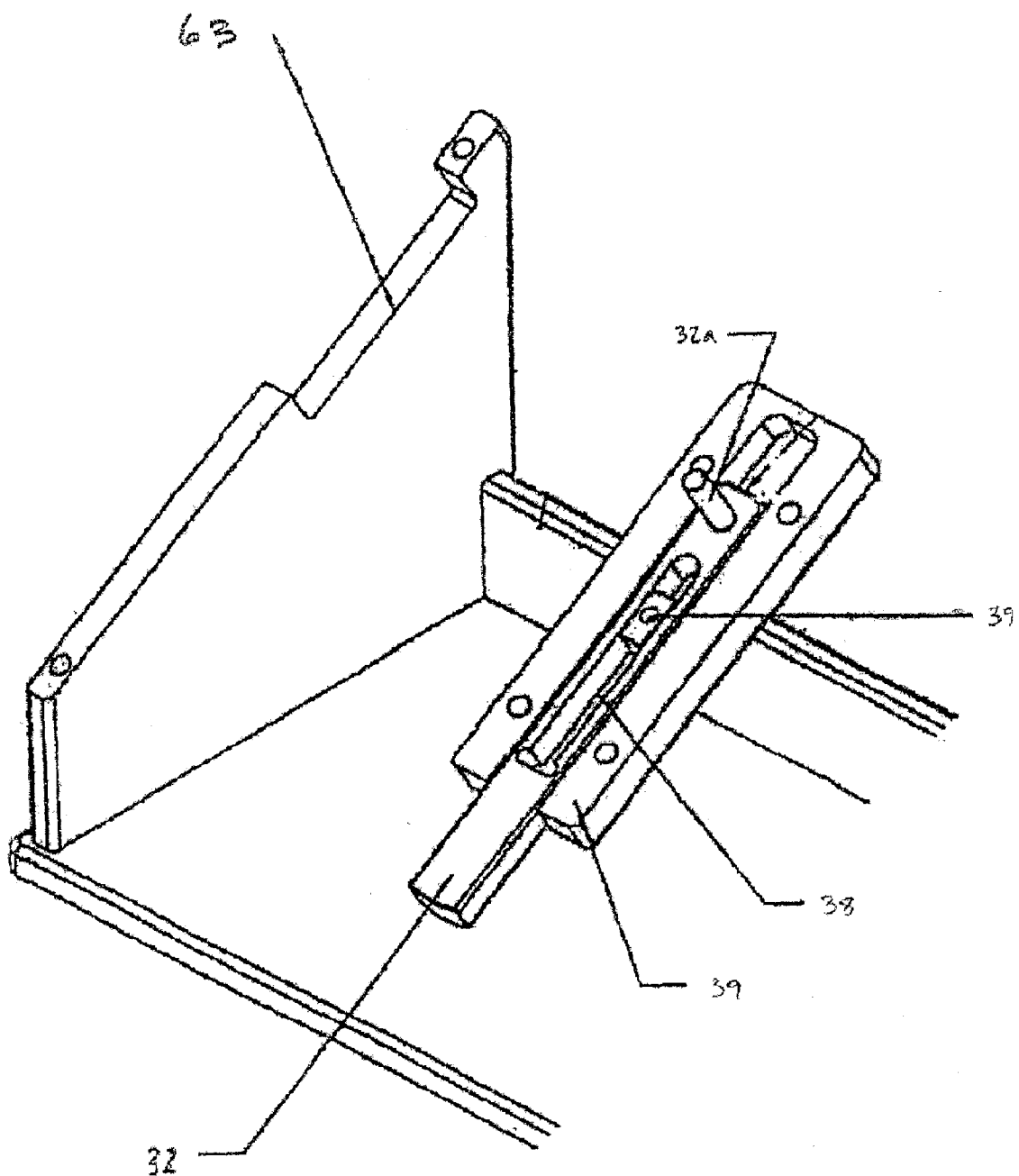
FIG. 3 is a cut-away illustration of the indexing member of the present invention illustrated in FIG. 1.

The indexing member 32 is spring-loaded and operatively engages the slidable cartridge holder 33 to select at least one cartridge from the plurality of cartridges 34*a* and 34*b*. As illustrated in FIG. 3, indexing member 32 includes a spring 38 and a dowel pin 32*a*. The indexing member 32 is slidably mounted on index support plate 39. Index support plate 39 has an integrated stop 39*a* to provide an end point to condense spring 38, thus forcing indexing member 32 to its resting position. The index support plate 39 is mounted to the underside of mounting plate 60, thereby permitting dowel pin 32a to engage the plurality of cartridges 34a and 34b to release an isotope seed or spacer, respectively.

As FIG. 1 illustrates, the viewing member 40 of the present invention further includes a body 41, a visualization plate 42, and a needle holder securement 43. The body 41 also includes a demarcation gauge 44 that permits identification of the number of isotope seeds and spacers to be loaded. The body 41 further accommodates the push rod guide member 24 and allows for the fixing of the visualization plate 42 by knobs 45, retaining clips 46, and lens clips 47. The visualization plate 42 allows for visualization of the demarcation gauge 44 while functioning as a radiation shield. Additionally, the needle holder securement 43 of the assembly accommodates the needle holder group 50.

Figure 4:
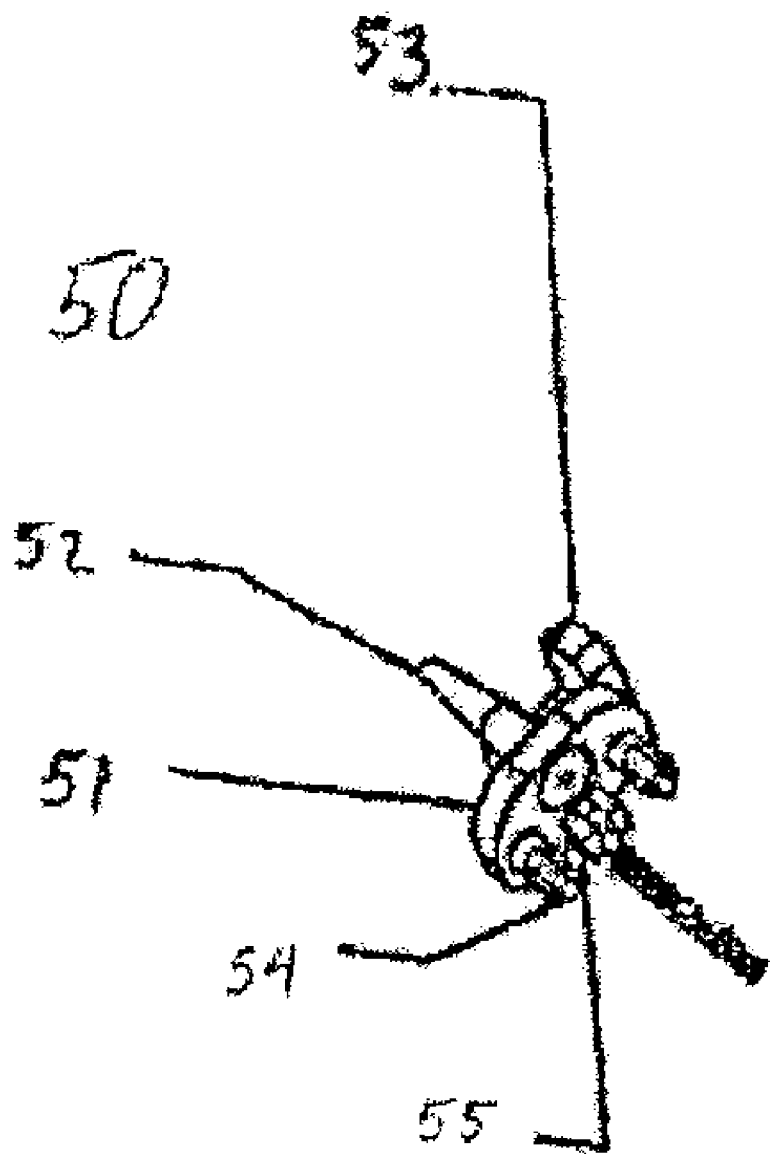
FIG. 4 is an illustration of the needle holder group of the present invention illustrated in FIG. 1.

As illustrated in FIG. 4, needle holder group 50 is composed of a needle holder flange 51, a needle holder hub 52, and a needle lock 53. The needle holder flange 51 is affixed to the needle holder securement 43 by screws 54 and dowel pin 55 and accommodates the needle holder hub 52 that further accommodates a needle. The needle is secured by the needle lock 53.

The preferred embodiment of the present invention semi-automatically and sequentially loads radioactive seed units and biocompatible spacer units into a brachytherapy device using the plurality of cartridges 34, with a plurality of aligned units contained therein, that is in operative engagement with the cartridge holder 33. A first cartridge is selected from the plurality of cartridges 34, and at least one unit of the first cartridge is deposited into a unit channel. The unit of the first cartridge is driven along the unit channel to a first predetermined point by the push rod 22, as visualized using demarcation gauge 44. A second cartridge is then selected from the plurality of cartridges 34, with at least one unit of the second cartridge also deposited into the unit channel. The unit of the second cartridge is also driven along the unit channel to a second predetermined point by the push rod 22, again as visualized using demarcation gauge 44. The unit of the first cartridge and the unit of the second cartridge are subsequently driven by the push rod 22 through needle holder hub 52 and inserted into a needle for insertion into biological tissue.

Figure 5:
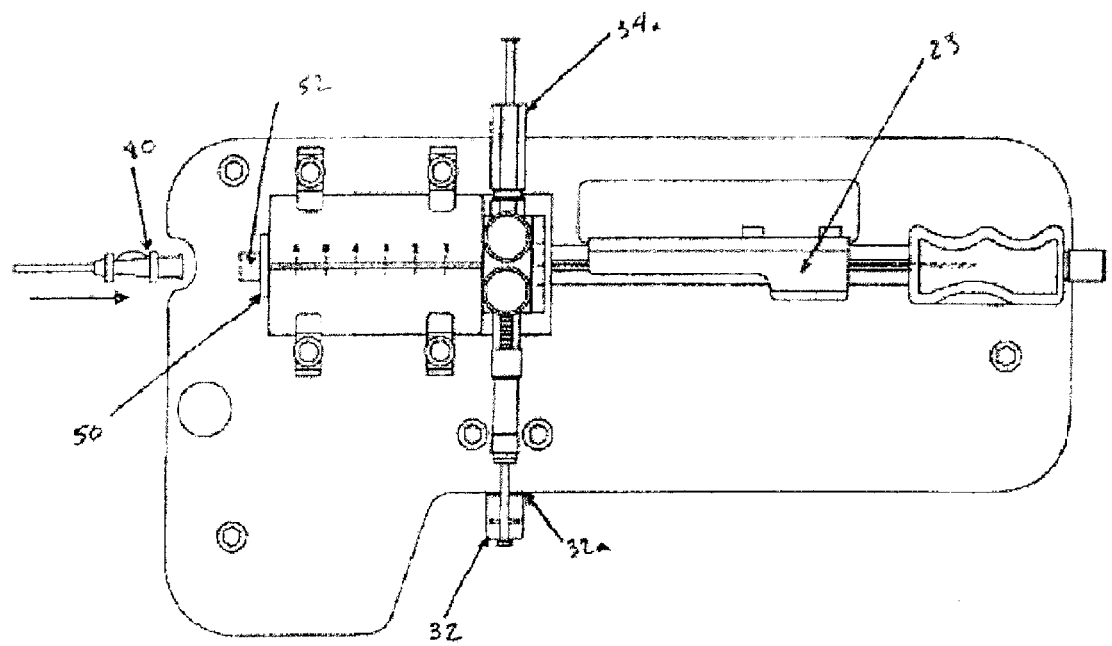
FIG. 5 is an illustration of one aspect of the operation of the preferred embodiment of the present invention.

FIGS. 5–10 illustrate the operation of semi-automatic needle loader assembly 10. As shown in FIG. 5, a needle assembly 80 is inserted into needle holder group 50 and secured by needle holder hub 52. As is further shown in FIG. 5, indexing member 32 is situated in a position, marked by indicator line 32a, which provides a user with a visual cue that neither an isotope seed nor a spacer has been selected for insertion.

Figure 6:
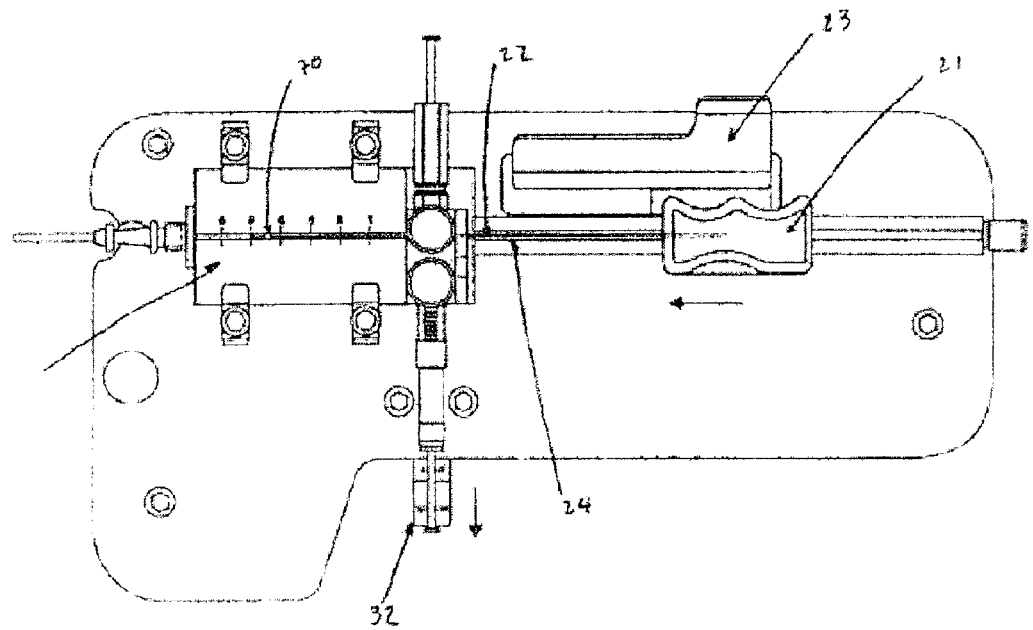
FIG. 6 is an illustration of another aspect of the operation of the present invention of FIG. 5.
Figure 7:
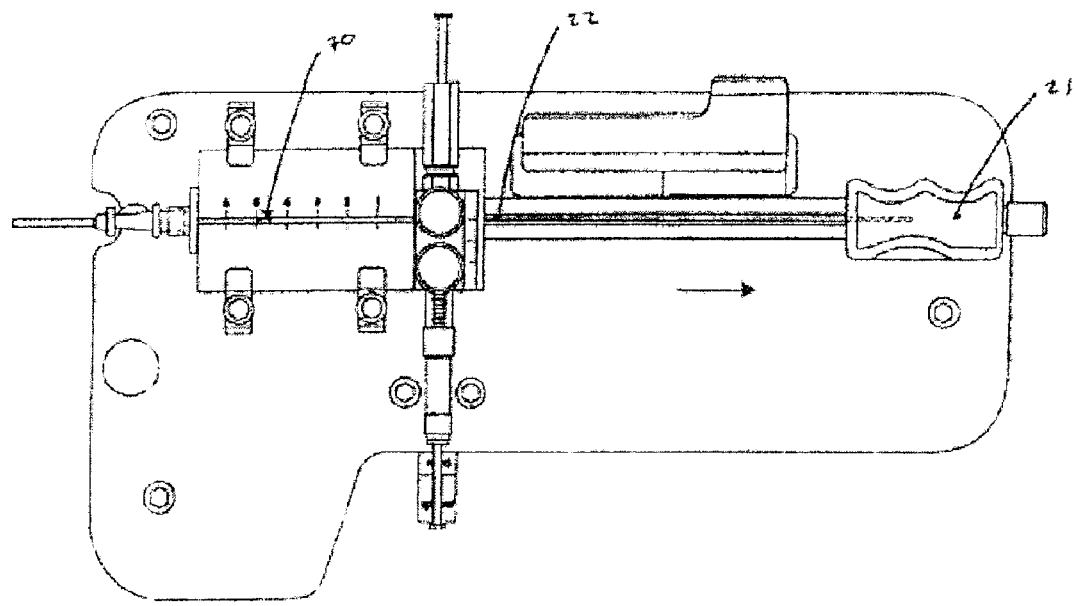
FIG. 7 is an illustration of still another aspect of the operation of the present invention of FIG. 5.
Figure 8:
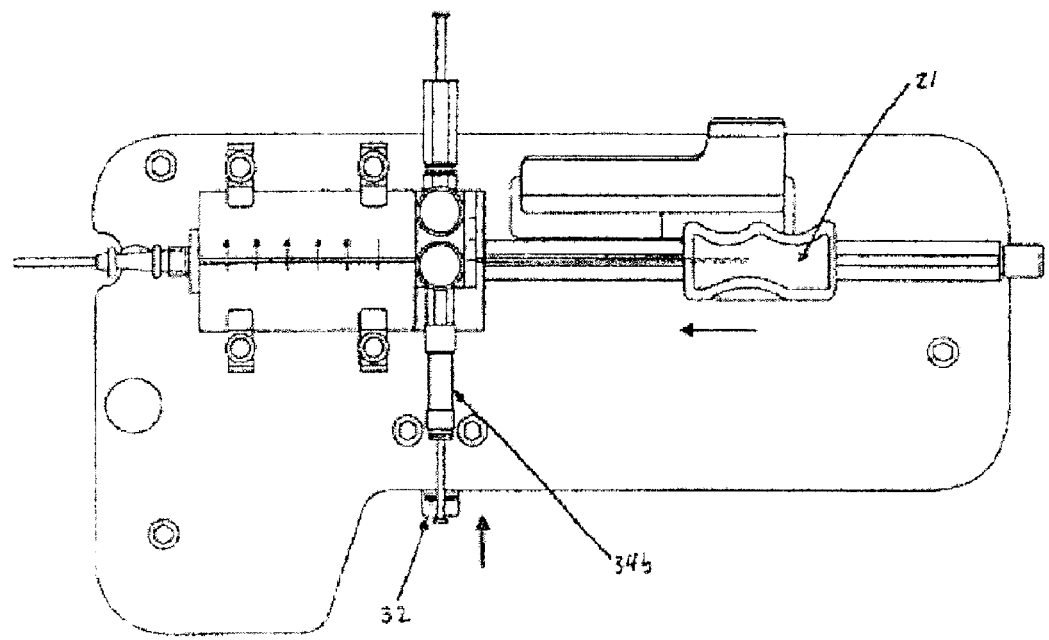
FIG. 8 is an illustration of yet another aspect of the operation of the present invention of FIG. 5.
Figure 9:
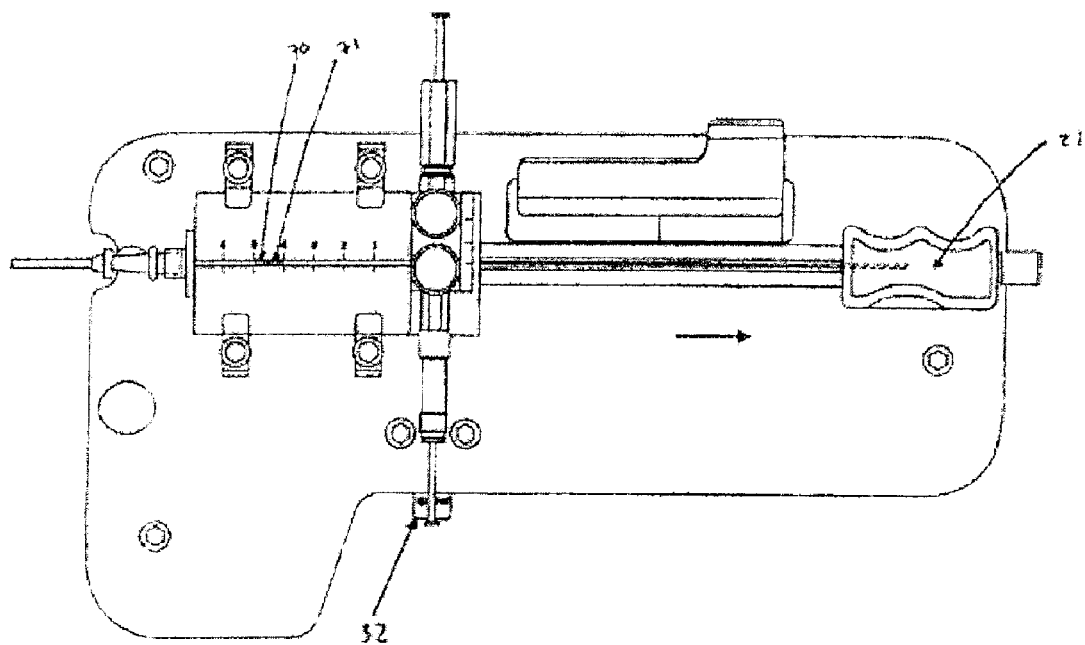
FIG. 9 is an illustration of another aspect of the operation of the present invention of FIG. 5.

FIG. 6 illustrates the process for selecting and positioning an isotope seed in accordance with the preferred embodiment of the present invention. As shown in FIG. 6, indexing member 32 is positioned to select an isotope seed. Once indexing member 32 is properly positioned, the user engages cartridge 34a for housing isotope seeds. By engaging cartridge 34a, isotope seed 70 is deposited in push rod guide member 24. Upon placement in push rod guide member 24, the user positions stop block member 23 out of the pathway of handle 21 so as to permit push rod 22 to travel a distance determined by the user and visualized at demarcation gauge 44. As illustrated in FIG. 7, once the user positions isotope seed 70 in the desired position, which can be viewed through demarcation gauge 44, the user then withdraws handle 21. The withdrawal of handle 21 causes push rod 22 to be withdrawn as well, thus leaving isotope seed 70 in the desired position. Further, as shown in FIG. 8, indexing member 32 can then be engaged to select a spacer from cartridge 34b. As with the selection of an isotope seed, once indexing member 32 is properly positioned, the user engages cartridge 34b for housing spacers. By engaging cartridge 34b, spacer 70 is deposited in push rod guide member 24. Upon placement in push rod guide member 24, again engages handle 21 so as to permit push rod 22 to travel a distance determined by the user and visualized at demarcation gauge 44. As illustrated in FIG. 9, once the user positions spacer 71 in the desired position in relation to isotope seed 70, which again can be viewed through demarcation gauge 44, the user then withdraws handle 21. The withdrawal of handle 21 causes push rod 22 to be withdrawn as well, thus leaving isotope seed 70 and spacer 71 in their desired positions.

Figure 10:
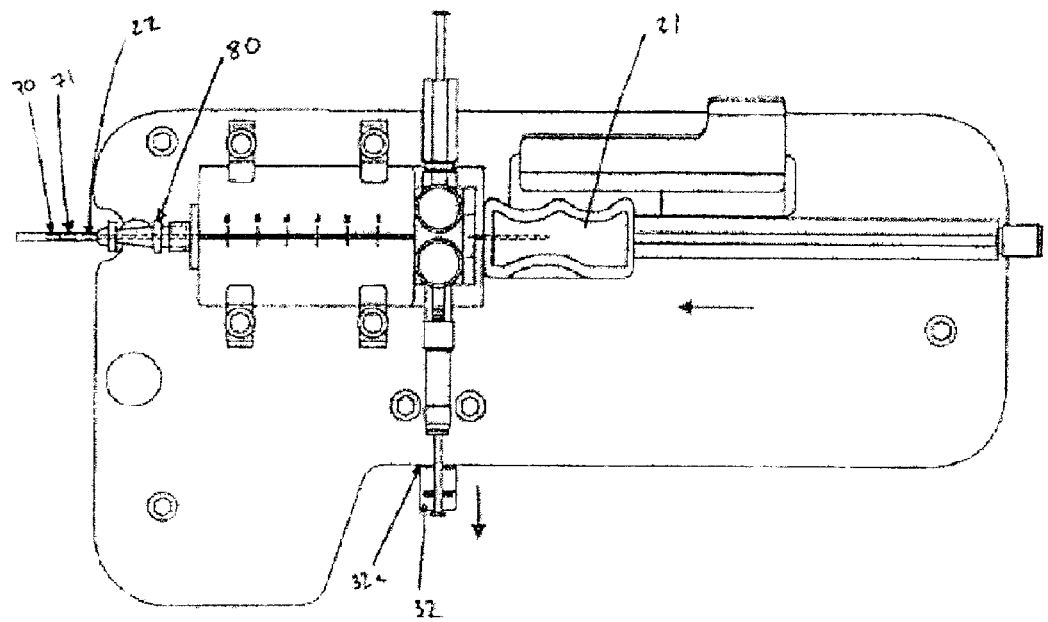
FIG. 10 is an illustration of still another aspect of the operation of the present invention of FIG. 5.

Once the desired number of isotope seeds and spacers are properly positioned, they can be inserted into needle assembly 80, as is illustrated in FIG. 10. In order to position isotope seed 70 and spacer 71 in needle assembly 80, indexing member 32 is situated in the position marked by indicator line 32a, which provides a user with a visual cue that neither an isotope seed nor a spacer has been selected for insertion. The user then engages handle 21 so as to permit push rod 22 to travel a distance into needle assembly 80. By doing so, isotope seed 70 and spacer 71 are placed in needle assembly 80. Handle 21 is subsequently withdrawn, causing push rod 22 to be withdrawn as well, thus leaving isotope seed 70 and spacer 71 in their desired positions within needle assembly 80 for insertion into a recipient.

Although only a few exemplary embodiments of the present invention have been described in detail above, those skilled in the art will readily appreciate that numerous modifications are to the exemplary embodiments are possible without materially departing from the novel teachings and advantages of this invention. Accordingly, all such modifications are intended to be included within the scope of this invention as defined in the following numbered claims.

What is claimed is:

1. A semi-automatic needle loader assembly comprising:
   a setting group for positioning at least one of an isotope seed and a spacer;
   a loading group operatively engaging said setting group for depositing said at least one of an isotope seed and a spacer;
   a viewing member for visualizing said at least one of an isotope seed and a spacer;
   a needle holding group positioned to pass said at least one of an isotope seed and a spacer to a needle assembly; and
   a handle and a push rod having a push rod guide member, the push rod operatively engaged with the handle and slidable within the push rod guide member, said push rod guide member passing through a stop block member and the stop block member being slidably mounted on a mounting plate.

2. The assembly according to claim 1, wherein the stop block member slidable selects a seed number.

3. The assembly according to claim 2 wherein the seed number indicates a number of isotope seeds.

4. The assembly according to claim 1, wherein the stop block member slidably selects a spacer number.

5. The assembly according to claim 4, wherein the spacer number indicates at least one biocompatible spacer.

6. The assembly according to claim 1, wherein the stop block member slidably selects a combined isotope seed and spacer number.

7. The assembly according to claim 1, wherein the stop block member is a distal endpoint for the handle in operative engagement with the push rod.

8. The assembly according to claim 1, wherein the loading group further comprises a loading block and an indexing member.

9. The assembly according to claim 8, wherein the loading block accommodates a slidable cartridge holder.

10. The assembly according to claim 9, wherein the slidable cartridge holder can hold a plurality of cartridges.

11. The assembly according to claim 10, wherein the plurality of cartridges includes at least one isotope seed cartridge.

12. The assembly according to claim 10, wherein the plurality of cartridges includes at least one spacer cartridge.

13. The assembly according to claim 8, wherein the loading block includes an alignment visualizer.

14. The assembly according to claim 13, wherein the alignment visualizer provides visual confirmation of a selected cartridge.

15. The assembly according to claim 8, wherein the indexing member operatively engages the slidable cartridge holder to select at least one cartridge from the plurality of cartridges.

16. The assembly according to claim 15, wherein the indexing member is spring-loaded.

17. A semi-automatic needle loader assembly comprising:
a setting group for positioning at least one of an isotope seed and a spacer;
a loading group operatively engaging said setting group for depositing at least one of an isotope seed and a spacer;
a viewing member comprising a body having a demarcation gauge, a visualization plate connected to said body, the viewing member constructed to permit visualizing at least one of an isotope seed and a spacer and a needle holder securement connected to said body; and
a needle holding group positioned to pass at least one of an isotope seed and a spacer to a needle assembly.

18. The assembly according to claim 17, wherein the demarcation gauge permits identification of a seed number.

19. The assembly according to claim 17, wherein the demarcation gauge permits identification of a spacer number.

20. The assembly according to claim 17, wherein the body further includes the push rod guide.

21. The assembly according to claim 17, wherein the visualization plate is affixed to the body.

22. The assembly according to claim 21, wherein the visualization plate allows for visualization of the demarcation gauge.

23. The assembly according to claim 22, wherein the visualization plate is clear.

24. The assembly according to claim 22, wherein the visualization plate is opaque.

25. The assembly according to claim 22, wherein the visualization plate is a radiation shielding material.

26. The assembly according to claim 17, wherein the needle holder securement accommodates an inserting group.

27. The assembly according to claim 26, wherein the inserting group further comprises; a needle holder flange; a needle holder hub connected to said needle holder flange; and a needle lock connected to said needle holder flange.

28. The assembly according to claim 27, wherein the needle holder flange is affixed to the needle holder securement.

29. The assembly according to claim 28, wherein the needle holder flange accommodates the needle holder hub.

30. The assembly according to claim 29, wherein the needle holder hub accommodates a needle.

31. The assembly according to claim 30, wherein the needle is secured by the needle lock.

* * * * *